United States Patent [19]

Alexson

[11] Patent Number: 4,806,730
[45] Date of Patent: Feb. 21, 1989

[54] METHOD OF FORMING CRISP WHITE INDICIA IN ALUMINUM

[75] Inventor: Charles E. Alexson, Blackbrook Township, Polk County, Wis.

[73] Assignee: Minnesota Mining and Manufacturing Company, St. Paul, Minn.

[21] Appl. No.: 118,046

[22] Filed: Nov. 9, 1987

Related U.S. Application Data

[62] Division of Ser. No. 847,483, Apr. 3, 1986, Pat. No. 4,736,742.

[51] Int. Cl.$^4$ .............................................. B23K 26/00
[52] U.S. Cl. ................................ 219/121.69; 156/643
[58] Field of Search ................. 219/121 LH, 121 LJ; 427/53.1; 346/76 L; 156/643

[56] References Cited

U.S. PATENT DOCUMENTS

| | | | |
|---|---|---|---|
| 4,304,981 | 12/1981 | Gappa | 219/121 LJ X |
| 4,335,295 | 6/1982 | Fowler | 219/121 LJ X |
| 4,370,542 | 1/1983 | Mills et al. | 219/121 LJ X |
| 4,626,656 | 12/1986 | Ootsuka et al. | 219/121 LP X |

Primary Examiner—C. L. Albritton
Attorney, Agent, or Firm—Donald M. Sell; Walter N. Kirn; Stephen W. Bauer

[57] ABSTRACT

An air motor driven device adapted for driving tools used during orthopedic surgery by rotating a driven shaft on the tool. The device has first and second spaced parallel output shafts driven at different speeds, at least one of which shafts can releasably engage the driven shaft of the tool. The second shaft has a through central opening accessible from its end opposite its output end so that the device can power pin or wire drivers or reamers guided on a guide wire. An attachment mechanism for releasably attaching a tool to the device is provided which receives an oval portion of the tool in a mating socket, and in addition to trigger operated valves for operating the air motor, provides a valve for shutting off or throttling the gas inlet line.

3 Claims, 6 Drawing Sheets

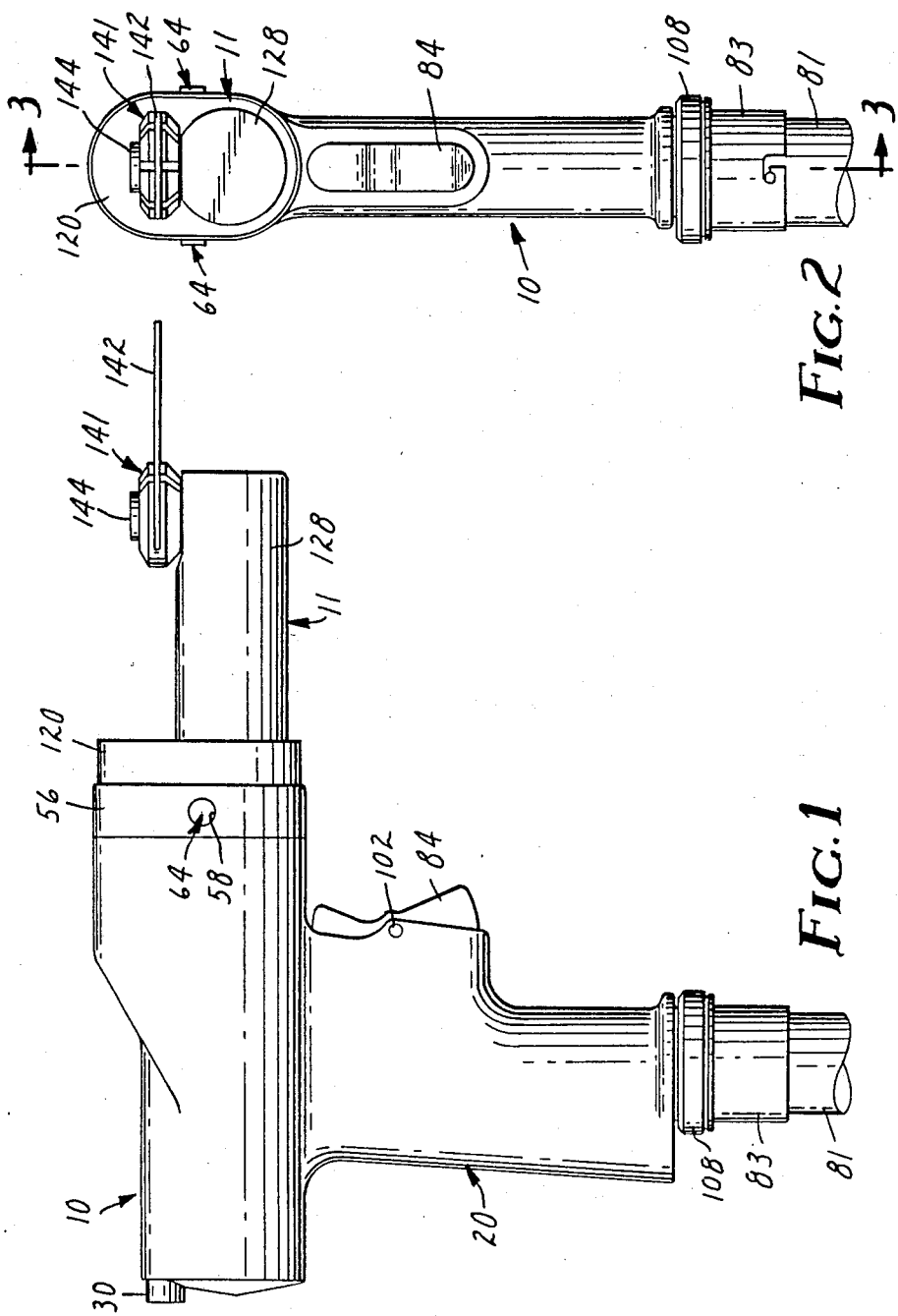

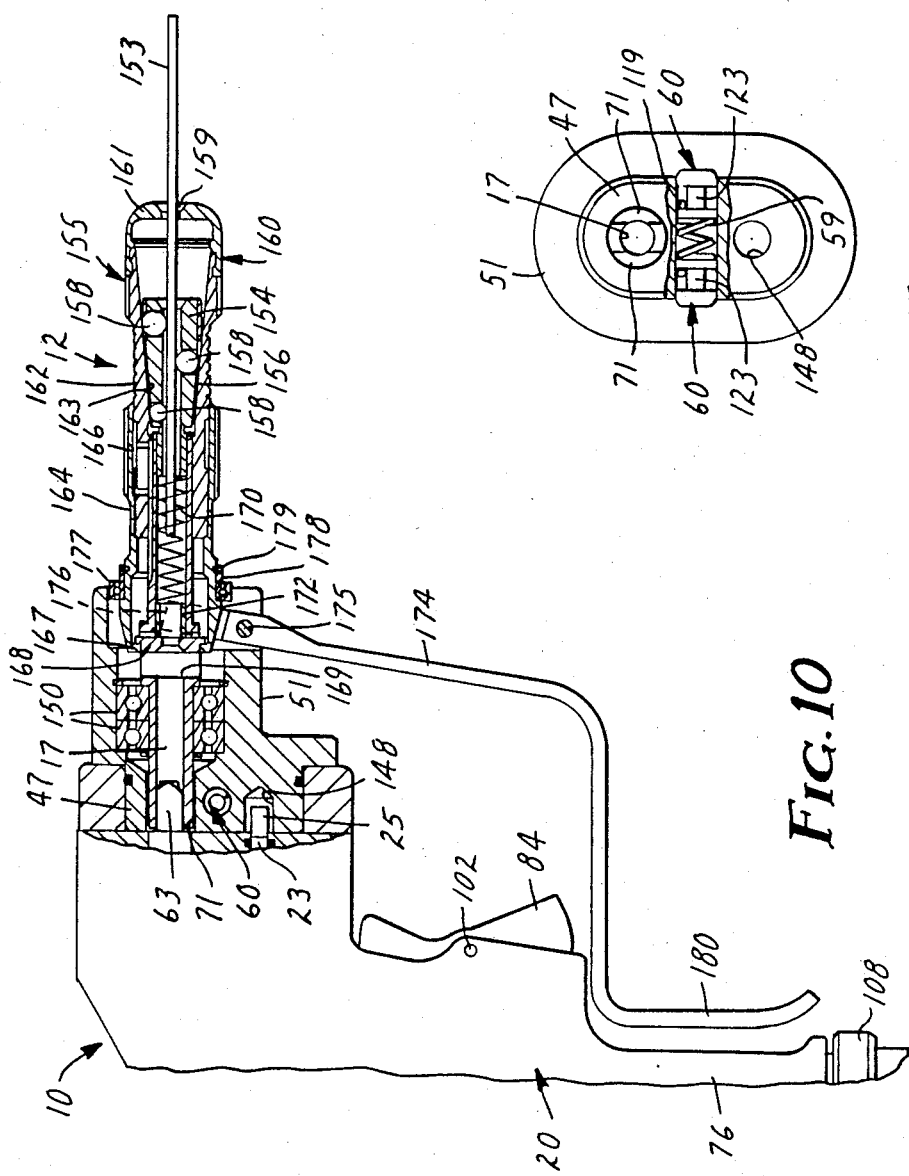

METHOD OF FORMING CRISP WHITE INDICIA IN ALUMINUM

This is a division of application Ser. No. 847,483 filed Apr. 3, 1986, which issued Apr. 12, 1988, as U.S. Pat. No. 4,736,742.

TECHNICAL FIELD

This invention relates to devices adapted to drive tools such as saws, pin or wire drivers, universal chucks and reamer drivers used in orthopedic surgery.

BACKGROUND ART

Several prior art devices are known which include a variable speed air motor for driving different rotatable shaft driven tools used in orthopedic surgery such as saws, pin or wire drivers, universal chucks and reamer drivers. While at least one of the prior art devices is able to adequately drive each such known tool, all such known prior art devices have lacked the degree of versatility that might be desired to properly drive all of the different tools that are used during various orthopedic procedures.

For example, hertetofore, many such devices have provided only one output shaft driven at a single speed ratio with respect to the speed of the air motor which limits the range of speeds available at that output shaft to drive different tools. While one such known device available from Howmedica, Rutherford, N.J., and known as the "Chirodrill" ™ provides two concentric output shafts driven at different speed ratios with respect to the speed of its air motor and thus provides two substantially different ranges of output speeds by which tools can be driven (e.g., a high output speed range at one shaft and a substantially lower output speed drive range at the other shaft), that device does not provide a cannulated or hollow drive shaft so that procedures such as pin or wire driving or following a guide wire that require such a hollow drive shaft are prevented and the versatility of the device is restricted.

DISCLOSURE OF THE INVENTION

The present invention provides a versatile device including a variable speed air motor adapted for properly driving all of the different known rotatable shaft driven tools that are used during orthopedic surgery such as saws, pin or wire drivers, universal chucks and reamer drivers; which device provides two output shafts driven at substantially different speed ratios with respect to the air motor to provide two different speed ranges for different tools to be driven, with the shaft providing the lower speed range being cannulated or hollow to facilitate using a wire or pin driver or follow a guide wire extending through a flexible reamer driven by the reamer driver.

According to the present invention there is provided a device adapted for driving tools used during orthopedic surgery by rotating at least one driven shaft on the tool, which device comprises an air motor mounted on a frame of the device; first and second spaced parallel output shafts each having an output end portion, at least one of which output shafts is adapted to releasably engage the driven shaft of the tool, with the second output shaft having a through central opening accessible from the end of the second output shaft opposite its output end; means for driving the output shafts from a rotor in the air motor with the second output shaft driven at a substantially slower rate of rotation (e.g., about 1000 R.P.M.) than the first output shaft (e.g. about 20,000 R.P.M.); means for releasably attaching the tool to the frame with the output end of at least one of the output shafts in driving engagement with the driven shaft of the tool; and means for coupling a supply of gas under greater than atmospheric pressure to the air motor to rotate the rotor.

In a preferred embodiment of the device, the means for driving the output shafts from the rotor includes the first output shaft being fixed to the rotor; a first drive gear coaxially fixed tothe first output shaft; a ring gear coaxialy fixed on the frame around the first drive gear; a plurality of planetary gears engaged with the first drive gear and ring gear in spaced relationship around the first drive gear and rotatably supported on a carrier rotatably mounted coaxially about the first output shaft so that the carrier is rotated by rotation of the drive and planetary gears, the carrier having a second drive gear coaxially fixed about its periphery; and a driven gear coaxially fixed to the second output shaft in engagement with the second drive gear. With this arrangement, the carier and its attached second drive gear will be caused to rotate at a slower speed than the first output shaft (e.g., about a 5/1 speed reduction) and the second drive gear and the driven gear can be sized to provide still further speed reduction to the second output shaft (e.g., about a 4/1 speed reduction) to produce a substantial overall speed reduction from the rotor to the second output shaft (e.g., about a 20/1 speed reduction).

Also, preferably the means for releasably attaching the tool to the frame with the driven shaft of the tool in engagement with the output end of the output shafts comprises walls of the frame defining a socket having an inlet opening and being adapted to receive a portion of a frame of the the tool in close fitting relationship. The walls defining the socket include an inner wall defining an inner end surface of the socket opposite its inlet opening with the output shafts projecting through the end wall with their output end portions positioned within the socket, and a side wall projecting from the inner wall and defining a generally oval side surface for the socket extending generally parallel to the axes of the output shafts between the bottom surface and the inlet opening. Engagement of the oval portion of the frame of the tool with the oval side surface of the socket provides firm engagement therebetween that will preclude relative rotation between the frames of the device and the tool during application of power from the device to drive the tool. Means are provided for releasably attaching the tool to the frame which comprise the side wall having opposed through openings adapted to receive locking pins biased to project outwardly from the frame portion of the tool adapted to be received in the socket, and release buttons having inner ends adjacent the socket and opposite outer ends accessible from the outer surface of the side wall. The release buttons are mounted in the through openings for movement between a lockable position with the inner ends of the buttons spaced from the side surface of the socket to receive the locking pins of the tool in the through openings to lock the tool to the device, and a release position to which the buttons may be moved by manual engagement with the outer ends of the buttons at which release position the inner ends of the buttons are aligned with the side surface of the socket and the tool may be separated from the device. The side surface of the socket is beveled outwardly adjacent the inlet openings to cam the outwardly biased locking pins onto the side surface when the frame portion of the tool is inserted into the socket and the output and driven shafts are adapted to automatically align with and engage each other so that a tool can be fully attached to the device by simply pressing the frame portion of the tool into the socket.

As is conventional, the means for coupling a supply of gas under greater than atmospheric pressure to the air motor to rotate the rotor comprises means for defining first and second passageways each having an outlet end in the air motor positioned so that gas directed through the first passageway into the motor causes rotation of the rotor in one direction and gas directed through the second passageway into the air motor causes rotation of the rotor in the opposite direction; means for defining an inlet passageway having an inlet end adapted to be releasably coupled to a source of gas under pressure and having an outlet end; and main valve means between the outlet end of the inlet passageway and the inlet end of the first and second passageways which are adapted to be manually actuated between opened and closed positions by pulling a trigger to direct gas from the inlet passageway into a selected one of the first and second passageways.

Additionally, the present invention provides a novel regulating valve means in the inlet passageway between its inlet and outlet ends which is infinitely adjustable between its open and closed positions for regulating the flow of air through the inlet passageway so that the air can be totally shut off as a safety measure to prevent operation of the device, or can be turned completely on to afford operation of the motor on the device at its maximum speed, or can be throttled to regulate the maximum speed of the motor on the device.

As illustrated, the regulating valve means in the inlet passageway comprises wall means for defining a portion of the inlet passageway and further defining a guide passageway extending transverse of the inlet passageway; a spool having end portions slidably mounted in the guide passageway for longitudinal sliding movement and being in airtight engagement with the wall means, and having a central portion of reduced cross section, the spool being longitudinally slidable in the guide passageway between an on position with the central portion extending across the inlet passageway to afford full flow of gas through the inlet passageway, and an off position with the central portion spaced from the inlet passageway and one of the end portions blocking the inlet passageway, with some positions of the spool between the on and off position restricting to varying degrees the flow of gas through the inlet passageway; andmanually operable means for positioning the spool in its on position to its off position or any position therebetween. Preferably, the wall means defining the portion of the inlet passageway and the guide passageway have opposite outer surfaces with the guide passageway opening through the outer surfaces, the end portions of the spool extend to at least the outer surfaces and at least one of the end portions projects beyond one of the outer surfaces in all positions of the spool, and the manually operable means for positioning the spool comprises a cam rotatably mounted on the frame and having cam surfaces adapted for engagement with the ends of the spool for moving the spool between its off and on positions upon manual rotation of the cam.

BRIEF DESCRIPTION OF THE DRAWING

The present invention will be further described with reference to the drawing wherein like numerals refer to like parts in the several figures, and wherein:

FIG. 1 is a vertical side view of a device according to the present invention shown coupled to a fragment of a hose providing a source of gas under pressure by which the device is powered, with a tool in the form of an orthopedic bone saw engaged with the device;

FIG. 2 is a vertical front view of the device, hose fragment, and tool shown in FIG. 1;

FIG. 10 is a fragmentary vertical view, partially in section, showing a tool in the form of a pin or wire driver attached to the device of FIG. 1;

FIG. 11 is an enlarged end view of the tool of FIG. 10 removed from the device with a part broken away to show detail;

FIG. 16 is a fragmentary cross-sectional view through a portion of a frame of the device, illustrating indicia formed by a method of this invention.

DETAILED DESCRIPTION

Figure 14:
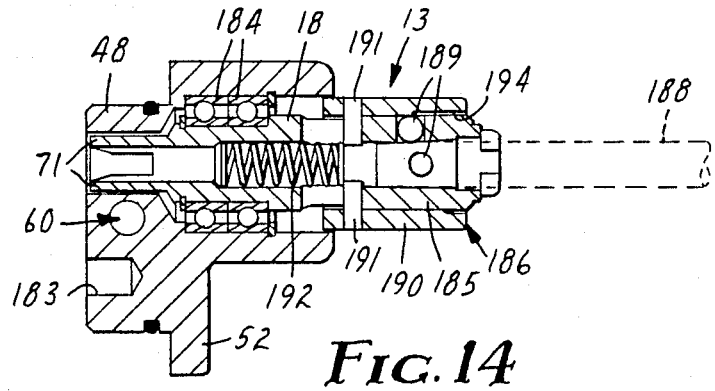
FIG. 14 is a vertical sectional view of a univesal chuck adapted to drive various cutting devices and adapted to releasably engage the device shown in FIG. 1.
Figure 15:
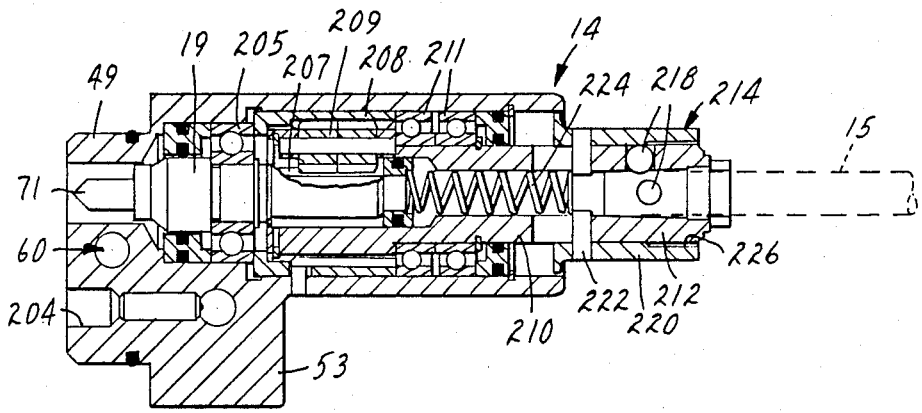
FIG. 15 is a vertical sectional view of a reamer driver adapted to drive a reamer and to releasably engage the device shown in FIG. 1.

Referring now to the drawing there is shown a gas operated device 10 (FIGS. 1 through 9) according to the present invention for driving tools used in orthopedic surgery, such as the bone saw 11 shown in FIGS. 1, 2, 12 and 13, the pin or wire driver 12 shown in FIGS. 10 and 11, the universal chuck 13 for driving cutting tools shown in FIG. 14 and the reamer driver 14 shown in FIG. 15 for use in driving reamers 15 or the like, which tools 11, 12, 13 and 14 are driven by rotating a driven shaft on the tool over a predetermined speed range (i.e. driven shafts 16, 17, 18 or 19 in the tools 11 through 14, respectively).

Figure 3:
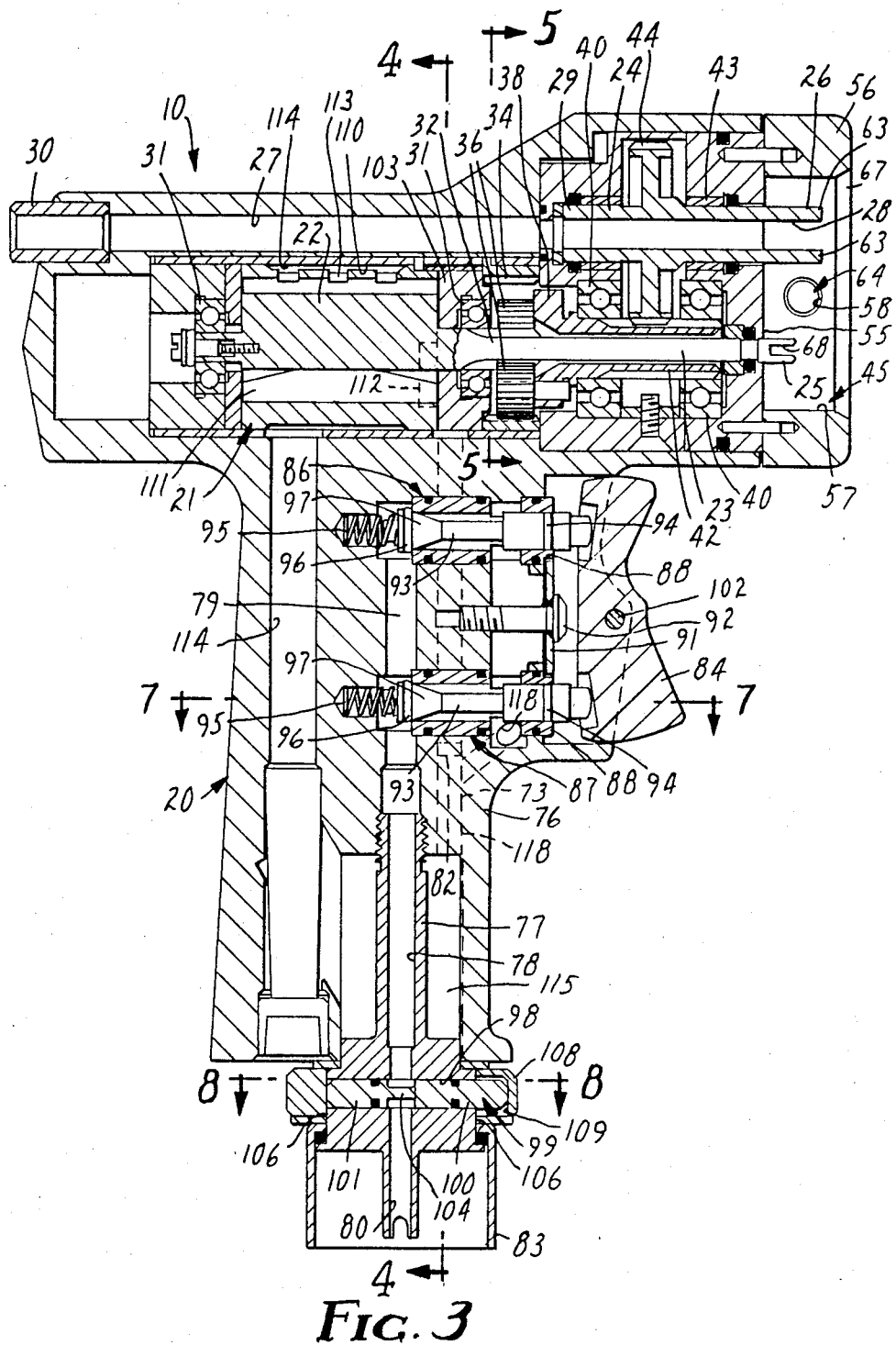
FIG. 3 is an enlarged sectional view taken approximately along line 3—3 of FIG. 2, but in which the hose and tool are not shown.

As is best seen in FIG. 3, the device 10 comprises a frame 20, an air motor 21 mounted on the frame 20 comprising a rotor 22, first and second spaced axially parallel output shafts 23 and 24 each having an output end portion 25 and 26 respectively adapted to releasably engage the driven shaft 16, 17, 18, or 19 of one of the tools 11, 12, 13, or 14, with the second shaft 24 having a through central opening 28 accessible from an end 29 of the second shaft 24 opposite its output end 26 through an opening 27 through the frame 20 partially defined by a hard steel cylindrical guide 30; means for driving the output shafts 23 and 24 from the rotor 22 to rotate both of the output shafts 23 and 24 with the second output shaft 24 rotating at a substantially slower rate of rotation than the first output shaft 23 upon rotation of the rotor 22; means for releasably attaching one of the tools 11, 12, 13, or 14 to the frame 20 with the driven shaft 16, 17, 18 or 19 of the tool in driving engagement with the output end 25 or 26 of one of the output shafts 23 and 24; and means for coupling a supply of gas under greater than atmospheric pressure to the air motor 21 to rotate the rotor 22.

As is best seen in FIG. 3, the means for driving the output shafts 23 and 24 from the rotor 22 includes the first output shaft 23 being fixed to (as by being an integral part of) the rotor 22 and with the rotor 22 being rotatably mounted on the frame 20 by ball bearings 31; a first drive gear 32 coaxially fixed to (as by being integrally formed with) the first output shaft 23; a ring gear 34 fixed on the frame 20 coaxially around the first drive gear 32; a plurality of planetary gears 36 having teeth engaged with the teeth of the first drive gear 32 and ring gear 34 around the first drive gear 32; a carrier 38 having a central opening through which the first output shaft 23 projects, which carrier 38 is rotatably mounted on the frame 20 by ball bearings 40 coaxially about the first output shaft 23, rotatably supports the planetary gears 36 in spaced relationship around the first drive gear 32, and has a second drive gear 42 coaxially fixed about (as by being integrally formed on) its periphery; and a driven gear 44 coaxially fixed to (as by being formed on) the second output shaft 24 and having its teeth in engagement with the teeth of the second drive gear 42, which second output shaft 24 is rotatably mounted on the frame 20 by spaced sleeve bearings 43.

As is best seen in FIGS. 3, 6, 11 and 13 the means for releasably attaching one of the tools 11, 12, 13 or 14 to the frame 20 with the driven shaft 16, 17, 18 or 19 of the tool in engagement with the output end portion 25 or 26 of one of the output shafts 23 and 24 comprises walls of the frame 20 defining a socket 45 having an inlet opening and being adapted to receive a portion 46, 47, 48 or 49 of a frame 50, 51, 52, or 53 of the tool 11, 12, 13, or 14 in close fitting relationship. Those walls include an inner wall defining an inner end surface 55 of the socket 45 opposite its inlet opening with the output shafts 23 and 24 projecting through the inner wall and the output end portions 25 and 26 of the output shafts 23 and 24 being positioned within the socket 45, and a side wall 56 fixed to and projecting from the inner wall and defining a generally oval side surface 57 for the socket 45 extending generally parallel to the axes of the output shafts 23 and 24 between the inner end surface 55 and the inlet opening of the socket 45, which generally oval side surface 57 has opposite end portions that are cylindrically arcuate about the axes of the output shafts 23 and 24.

Means are provided for releasably attaching one of the tools 11, 12, 13 or 14 to the frame 20 of the device 10. These means comprise the side wall 56 having opposed transverse stepped through openings 58 adapted to receive locking pins 60 biased by a spring 59 to project outwardly from the frame portions 46, 47, 48 or 49 of the tools 11, 12, 13 or 14 adapted to be received in the socket 45; and release buttons 64 in the through openings 58 having inner ends 65 adjacent the socket 45 and opposite outer ends 66 accessible from the outer surface of the side wall 56 and being mounted in the through openings 58 for movement (within limits defined by pins 61 fixed in the side wall 56 through transverse openings 62 in the buttons 64) between a lockable position to which the release buttons 64 are biased by springs 54, at which lockable position the inner ends 65 of the buttons 64 are spaced from the side surface 57 of the socket 45 to receive the locking pins 60 of the tools 11, 12, 13 or 14 in the through openings 58 to lock the tools 11, 12, 13 or 14 to the device 10; and a release position to which the buttons 64 may be moved by manual engagement with the outer ends 66 of the buttons 64 to press them toward each other at which the inner ends 65 of the buttons 64 are aligned with the side surface 57 of the socket 45 to remove the locking pins 60 from the through openings 58 so that the tools 11, 12, 13 or 14 may be separated from the device 10. The side wall 56 is beveled outwardly adjacent the inlet opening to the socket 46 to provide a beveled surface 67 that will cam the outwardly biased locking pins 60 onto the side surface 57 when the frame portions 46, 47, 48 or 49 of the tools 11, 12, 13, or 14 are inserted into the socket 45.

The output end portion 26 of the second output shaft 24 comprises two opposed circumferentially spaced tapered projections 63 adapted to engage between two similarly shaped spaced tapered projections 71 on the ends of the driven shafts 17, 18 and 19 of the tools 12, 13 and 14, with the tapered ends 63 and 71 causing proper alignment thereof as the second output shaft 24 and one of the driven shafts 17, 18 or 19 engage; whereas the output end portion 25 of the first output shaft 23 has a transverse slot 68 adapted to receive a transverse drive plate 69 (FIG. 12) in the driven shaft 16, which drive plate 69 is slidably mounted in a longitudinal slot diametrically across a socket in the driven shaft 16 and is biased toward the end of the shaft 16 by a spring 70 to afford improper alignment of the output end portion 25 and the drive plate 69 as the bone saw 11 engages the device 10 and subsequent engagement of the drive plate 69 with the slot 68 under the influence of the spring 70 as the fist output shaft 23 is rotated by the device 10.

Figures 4, 5, 6:
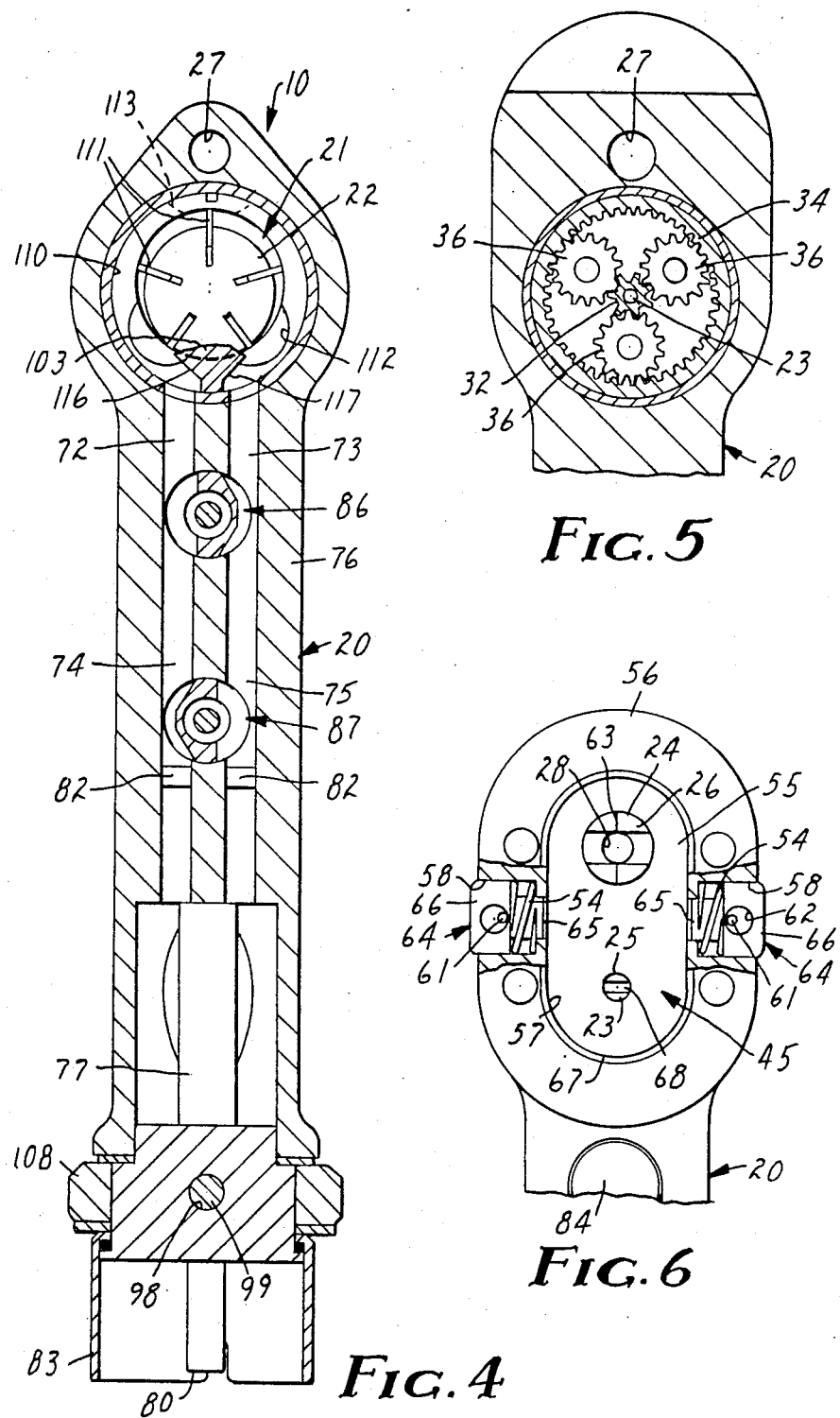
FIG. 4 is a sectional view taken approximately along line 4—4 of FIG. 3.
FIG. 5 is a fragmentary sectional view taken approximately along lines 5—5 of FIG. 3.
FIG. 6 is a fragmentary end view of the device as shown in FIG. 3 with a part broken away to show detail.
Figure 7:
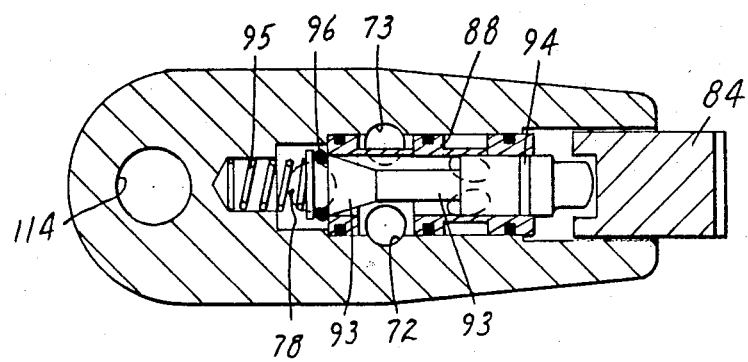
FIG. 7 is an enlarged sectional view taken approximately along line 7—7 of FIG. 3.
Figure 8:
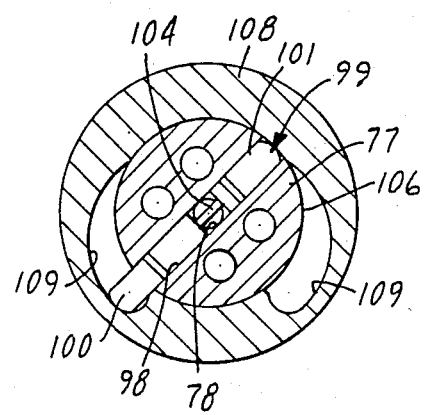
FIGS. 8 and 9 are sectional views taken approximately along line 8—8 of FIG. 3 showing a spool and a cam in on and off positions respectively.
Figure 9:
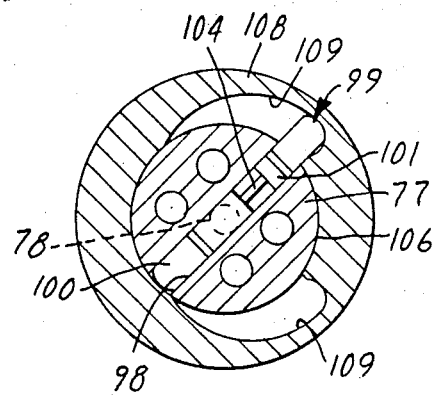
Figure 13:
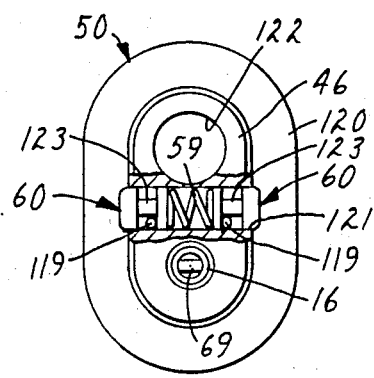
FIG. 13 is an enlarged end view of the bone saw shown in FIG. 12.
Figure 12:
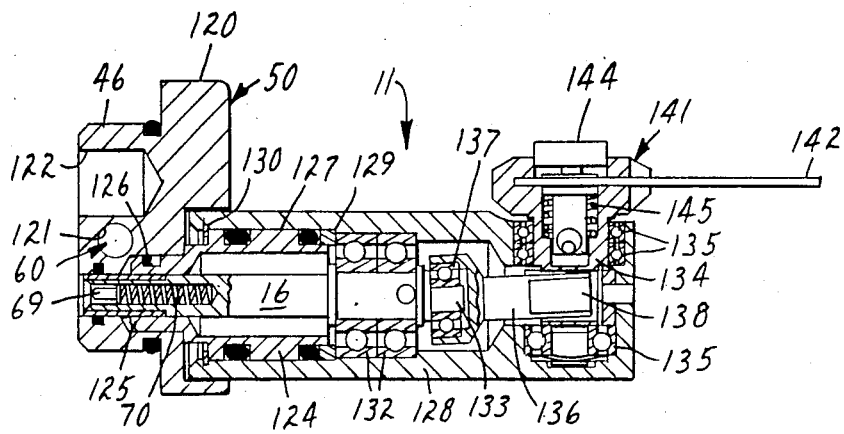
FIG. 12 is a vertical sectional view of the orthopedic bone saw shown in FIGS. 1 and 2.

The means for coupling a supply of gas under greater than atmospheric pressure to the air motor 21 to rotate its rotor 22 comprises (1) means in the form of the frame 20 and a pair of plugs 82 inserted in openings bored in the frame 20 for defining first and second passageways 72 and 73 (FIG. 4) each having inlet ends 74 and 75 respectively and having outlet ends in opposite sides of the air motor 21 for directing gas to different positions so that gas directed through the first passageway 72 into the air motor causes rotation of the rotor 22 in a first or clockwise direction as viewed in FIG. 4, and gas directed through the second passageway 73 into the air motor 21 causes rotation of the rotor 22 in a second direction opposite the first direction or counterclockwise as viewed in FIG. 4; (2) means in the form of the frame 20 including a generally tubular portion 77 thereof threaded into a main portion 76 of the frame 20 that defines a handle by which the device 10 is manually grasped, and an upper portion in which the air motor 21 and output shafts 23 and 24 are mounted, which tubular portion 77 (FIG. 3) defines the major part of an inlet passageway 78 having an outlet end 79 and an inlet end 80 adapted to be releasably coupled to a source of gas under pressure such as from a hose 81 (FIGS. 1 and 2) and a bayonet type quick disconnect portion on the hose 81 adapted to engage a mating portion 83 of the quick disconnect rotatably mounted about the tubular portion 77 of the frame 20; and (3) main valve means positioned between the outlet end 79 of the inlet passageway 78 and the inlet ends 74 and 75 of the first and second passageways 72 and 73 adapted to be activated by manually manipulating a trigger 84 between opened and closed positions for selectively directing gas from the inlet passageway 78 into one of the first and second passageways 72 and 73. Also, regulating valve means are provided in the inlet passageway 78 between its inlet and outlet ends 80 and 79 which are infinitely adjustable between open and closed positions for regulating the flow of air through the inlet passageway 78.

The main valve means comprises a pair of valve assemblies 86 and 87 each comprising (1) a housing member 88 sealed in the main portion 76 of the frame 20 by O-rings and held in place by a removable plate-like portion 91 of the frame 20 attached to its main portion 76 by a screw 92; (2) a plunger 93 axially slidably mounted in the housing member 88 and sealed in the housing member 88 by an O-ring 94, which plunger 93 is biased by a spring 95 to a position with an O-ring 96 around a head 97 on the plunger 93 in sealing engagement against a lip on the housing member 88 to prevent gas at the outlet end 79 of the inlet passageway 78 from passing into the first passageway 72 or the second passageway 73 which the valve assembly 86 or 87 controls. Either of the plungers 93 is movable to an open position by pivoting the trigger 84 in the appropriate direction around a pin 102 to move the plunger 93 and thereby the O-ring 96 on that plunger 93 away from its seat to allow gas under pressure to pass from the inlet passageway 78 into one of the passageways 72 or 73 to produce the desired direction of rotation of the rotor 22.

The regulating valve means in the inlet passageway 78 comprises wallmeans or walls of the frame portion 77 for defining both a part of the inlet passageway 78 and further defining a guide passageway 98 extending transverse of the inlet passageway 78; a spool 99 having end portions 100 and 101 slidably mounted in the guide passageway 98 for longitudinal sliding movement and having O-rings around their peripheries to place them in airtight sliding engagement with the frame portion 77, and a central portion 104 of reduced cross section. The spool 99 is longitudinally slidable in the guide passageway 98 between an on position (FIGS. 3 and 8) with the central portion 104 extending across the inlet passageway 78 to afford flow of gas through the inlet passageway 78; and an off position (FIG. 9) with the central portion 104 spaced from the inlet passageway 78 and the end portion 100 blocking the inlet passageway 78, with some positions of the spool 99 between its on and off positions restricting flow of gas through the inlet passageway 78; and manually operable means for positioning the spool 99 in any position including its on position and its off position and any position therebetween.

The wall means or portion 77 of the frame 20 defining the inlet passageway 78 and the guide passageway 98 have opposite arcuate outer surfaces 106 with the guide passageway 98 opening through the outer surfaces 106. The end portions 100 and 101 of the spool 99 extend to at least the outer surfaces 106 and at least one of the end portions 100 or 101 projects beyond one of the outer surfaces 106 in all positions of the spool 99. The manually operable means for positioning the spool 99 in any position including its on and its off position and any position therebetween comprises a cam 108 rotatably mounted on the tubular portion 77 of the frame 20, having cam surfaces 109 adapted for engagement with the end portions 100 and 101 of the spool 99 for moving the spool 99 between its off and on positions upon manual rotation of the cam 108 relative to the frame 20, and a knurled cylindrical periphery facilitating manual engagement of the cam 108 to rotate it.

The air motor 21 to which gas may be directed through the first and second passages 72 and 73 is of a known type comprising walls defining a generally cylindrical chamber 110 in which the rotor 22 is rotatably mounted about an axis spaced from the axis of the chamber 110. The rotor 22 has a plurality of radially extending slots in which plate-like vanes 111 are slidably positioned and will be biased by gas pressure in the motor 21 radially outwardly of the rotor 22 into slidable sealing engagement with the inner cylindrical surface defining the chamber 110. Gas directed into the chamber 110 through either the first or second passageways 72 or 73 enters through a passageway 116 or 117 defined by a plate 103 at the end of the rotor 22 adjacent the first output shaft 23 from which a major portion of the gas flows through a crescent shaped cavity 112 into the space between the rotor 22 and chamber 110 and moves with and drives the rotor 22 through about 180 degrees of its rotation where the gas escapes through slots 113 opening at the side of the motor 21 opposite the passageways 72 and 73 and through a cavity extending circumferentially around the motor 21 into an exhaust passageway 114 formed in the frame 20 and communicating between the cavity and an outlet opening to the atmosphere adjacent the tubular portion 77 of the frame 20 at the distal end of the handle for the device 10.

Some of the gas (a minor portion) moves with rotor 22 past the slots 113 and then is exhausted out the cavity 112 and passageway 72 or 73 through which pressurized gas is not being introduced to the motor 21, from which passageway 72 or 73 that gas escapes into the housing member 88 of the valve assembly 86 or 87 that is not open between the plunger 93 and housing member 88 of that not open valve assembly 86 or 87 into a passageway defined between the plate-like and main portions 91 and 76 of the frame 20 and through a passageway 118 into a chamber 115 around the tubular portion 77 that communicates with the main exhaust passageway 114.

The bone saw 11 shown in FIGS. 1, 2, 12 and 13 comprises its frame 50, a first part 120 of which has the already described projecting portion 46 adapted to be received in the socket 45 of the device 10. The projecting portion 46 has a transverse opening 121 in which are positioned the locking pins 60 adapted for releasable engagement with the openings 58 in the side wall 56 of the device 10, which pins 60 are biased outwardly by the spring 59 and are movable in the opening 121 within limits determined by engagement of a pin 119 anchored in the frame 50 with spaced inner surfaces of the pin 60 defined by a reduced diameter central portion 123 thereof between (1) outer positions shown at which outer ends of the pins 60 can enter the openings 58 to lock the frame 50 to the device 10, and (2) release positions with the pins 60 entirely within the opening 121 in the frame 50 at which the projecting portion 46 can be inserted in or removed from the device 10. The projecting portion 46 of the frame 50 also has a bore 122 adapted to provide clearance for the output end portion 26 of the second output shaft 24 which does not make driving engagement with the bone saw 11.

The frame 50 of the bone saw includes a second part 124 having a cylindrical end 125 fixed in a receptacle in the first frame part 120 by a transverse pin 126, and having a cylindrical periphery 127 about which a third part 128 of the frame 50 is rotatably journaled. The third frame part 128 is retained in place by a shoulder 129 and an internal outwardly spring biased retaining ring 130 engaging the second frame part 124 on opposite ends of the periphery 127, and is restricted against free rotation about the second frame part 124 by two O-rings compressed therebetween.

The driven shaft 16 on the bone saw 11 is rotatably mounted through a cavity defined in the first, second and third frame parts 120, 124 and 128 by two bearings 132, has an end in the projecting portion 46 carrying the transverse spring 70 biased drive plate 69 adapted to be engaged by the first output shaft 23 as has previously been described, and has an off center pin 133 projecting from its end opposite the drive plate 69. The pin 133 has a central axis that at all rotational positions of the driven shaft 16 intersects the axis of a drive member 134 mounted in the third frame part 128 by bearings 135 for pivotal movement about an axis at a right angle to the axis of the driven shaft 16. An orbiting link 136 has a concentric bearing 137 at one end engaged over the off center pin 133, and an opposite flatted end portion 138 with flats on both sides parallel to the pivot axis of the drive member 134. The flats on the flatted end portion 138 are closely received in a longitudinally extending slot in the drive member 134, which slot has sufficient length so that the link 136 can pivot in the slot in the plane defined by the axes of the driven shaft 16 and drive member 134. Thus only the movement of the axis of the link 136 out of that plane will cause movement of the drive member 134; that movement being an oscillating movement of the drive member 134 about its axis as the driven shaft 16 is rotated by the device 10.

The drive member 134 is included in an attaching assembly 141 for releasably attaching an osteomy blade 142, which attaching assembly 141 and blade 142 are more completely described in U.S. Pat. No. 4,386,609 incorporated herein by reference. As described more fully in U.S. Pat. No. 4,386,609, the blade 142 can be inserted or removed by depressing a locking button 144 included in the attaching assembly 141 against the bias of a spring 145. The third frame part 128 of the bone saw 11 may be rotated to any position around the cylindrical periphery 127 of the second frame part 124 to present the saw blade 142 at many orientations with respect to the device 10, as may be convenient during use of the bone saw 11 during surgery.

The pin or wire driver 12 shown in FIG. 10 comprises its frame 51 including the already described projecting portion 47 adapted to be received in the socket 45 of the device 10. The projecting portion 47 carries the locking pins 60 and their biasing spring 59, which pins 60 are adapted for releasable engagement with the openings 58 in the side wall 56 of the device 10, and has a bore 148 adapted to provide clearance for the output end portion 25 of the first output shaft 23 which does not make driving engagement with the wire driver 12.

The driven shaft 17 on the wire driver 12 projects through and is rotatably mounted in a cavity defined in the frame 51 by two ball bearings 150. Like the second output shaft 24, the driven shaft 17 has a through central opening, and has two tapered projections 71 on its end in the projecting portion 47 adapted to be engaged by the similar projections 63 on the output end portion 26 of the second output shaft 24 as has previously been described. On the end portion of the driven shaft 17 opposite the projections 71 is fixed (by threaded engagement) an inner portion 154 of a special chuck assembly 155 for driving pins or wires (such as a wire 153 illustrated) having drill like cutting surfaces on their leading ends. The inner portion 154 has a through central opening, a conically tapered outer surface 156 and three sets of three circumferentially spaced through openings from the outer surface to the central opening in which are positioned nine locking balls 158, three each of the same diameter. Also included in the chuck assembly 155 is an outer portion 160 including a cap-like end part 161 having a central opening 159 through its end wall, a front cylindrical part 162 to which is threadably and fixedly engaged the end part 161 and which has a conical inner surface 163 adapted to engage the outer surfaces of the locking balls 158. The outer portion 160 of the chuck assembly 155 also includes a rear cylindrical part 164 adjustably threadably engaged with the front part 162 at threads 166, having an annular inwardly projecting lip 167 at its end opposite the front cylindrical part 162 within which is engaged a transversely extending cross bar 168 with a central opening, which cross bar 168 extends radially through a transverse opening 169 in the driven shaft 17. The cross bar 168 is biased into engagement with the lip 167 by a spring 170 compressed in the driven shaft 17 between the inner portion 154 and a hollow cylindrical spacer 172 between the spring 170 and cross bar 168, thereby affording relative adjustment of the front and rear cylindrical parts 162 and 164 at the threads 166 and biasing the outer portion 160 of the chuck assembly 155 to its position relative to its inner portion 154 with the conical surface 163 spaced at its maximum possible distance from the locking balls 158.

A lever 174 is pivotably mounted on the frame 51 at a pin 175 and has a forked end part 176 engaging the outer race of a ball bearing 177 having its inner race fixed about the periphery of the rear cylindrical part 164 by a spacer 178 and snap ring 179. The lever 174 has an end portion 180 disposed adjacent and generally parallel to the front face of the handle of the device 10, which end portion 180 is adapted to be engaged by a user of the device 10 to move the lever 174 between a release position spaced from the handle at which the spring 170 provides the maximum possible separation between the conical surface 163 and the locking balls 158, and an engage position adjacent the handle (shown in FIG. 10) at which the lever 174 moves the outer portion 160 of the chuck assembly 155 away from the frame 51 of the wire driver 12 by a predetermined amount to decrease that spacing between the conical surface 163 and locking balls 158.

To use the wire driver 12, a user inserts the wire 153 through the central opening 159 in the end part 161, between the locking balls 158 in the central opening of the inner portion 154, and through the central opening in the spring 170, the spacer 172, the cross bar 168, the driven shaft 17, the second output shaft 24, and through the aligned opening 27 and guide 30 in the frame 20. The user then rotates the front cylindrical part 162 into the rear cylindrical part 164 of the outer portion 160 until its conical inner surface 163 presses the locking balls 158 against the wire 153 with the lever 174 in its release position. The user then adjusts the relative position of the front and rear cylindrical parts 162 and 164 until the wire 153 can be slid longitudinally through the chuck assembly 155 with the lever 174 in its release position, but will be firmly engaged by the locking balls 158 in the chuck assembly 155 when the lever 174 is moved to its engage position. In use, the user can then activate the device 10 by pulling the trigger 84 and move the lever 174 to its engage position by pulling its end portion 180 toward the handle to rotate the wire 153 from the chuck assembly 155, and can allow movement of the lever 174 to its release position under the influence of the spring 170 by releasing end portion 180 of the lever 174 to afford movement of the chuck assembly along the wire 153 to again engage a new portion thereof by movement of the lever 174 back to its engage position as is needed to drive the wire 153 into an object, such as a bone.

The universal chuck 13 shown in FIG. 14 comprises its frame 52 including the already described projecting portion 48 adapted to be received in the socket 45 of the device 10, which projecting portion 48 carries the locking pins 60 adapted for releasable engagement with the openings 58 in the side wall 56 of the device 10, and has a bore 183 adapted to provide clearance for the output end portion 25 of the first output shaft 23 which does not make driving engagement with the univesal chuck 13.

The driven shaft 18 of the universal chuck 13 projects through and is rotatably mounted in a cavity defined in the frame 52 by two ball bearings 184. Like the second output shaft 24, the driven shaft 18 has a through central opening, and has two tapered projections 71 on its end in the projecting portion 48 adapted to be engaged by the similar projections 63 on the second output shaft 24 as has previously been described. The end portion of the driven shaft 18 opposite the projections 63 provides an inner portion 185 of a special chuck assembly 186 adapted for engaging tools such as the rotary cutter 188 (e.g., a drill) shown in phantom outline in FIG. 14 which have driven ends of the types commercially designated "Hudson" or "Zimmer" TM style. The inner portion 185 has through radially extending passageways from its outer surface to its central opening in which are positioned locking balls 189. Also included in the chuck assembly 186 is a sleeve-like outer portion 190 to which are fixed opposed inwardly projecting pins 191 received in opposed longitudinal slots in the inner portion 185 and engaging the end of a compressed coil spring 192 centerally located in the driven shaft 18 and having its opposite end supported against an end wall of a socket in the driven shaft 18 to bias the sleeve-like outer portion 190 to a position at which its inner surface engages the outer surfaces of the locking balls 189 and can lock the balls 189 in engagement with recesses in the driven end of the cutter 188. The sleeve-like outer portion 190 can be manually moved axially relative to the driven shaft 18 to further compress the spring 192 and position grooves 194 on its inner surface adjacent the locking balls 189 so that they may move radially outwardly of the inner portion 185 and out of the recesses in the cutter 188 so that the cutter 188 may be removed or inserted.

To use the universal chuck 13, a user moves the sleeve-like outer portion 190 axially toward the frame 52 so that the locking balls 189 can move outwardly into the grooves 194, inserts the driven end of a tool such as the cutter 188 into the central opening of the inner portion 185, and releases the sleeve-like outer portion 190 so that the spring 192 positions its inner surface to lock the locking balls 189 in recesses in the tool thereby locking it in place. The driven shaft 18 including the inner portion 185 of the chuck assembly 186 and the spring 192 provide a through central opening so that a guide wire already positioned in an object (e.g., in a bone) can be fed through a central opening in the tool, the universal chuck 13 and the second output shaft 24 of the device 10, the device 10 can be activated, and the tool can be moved along the guide wire which then acts as a guide for the tool as it is moved through the object.

The reamer driver 14 shown in FIG. 15 comprises its frame 53 including the already described projecting portion 49 adapted to be received in the socket 45 of the device 10, which projecting portion 49 carries the locking pins 60 adapted for releasable engagement with the openings 58 in the side wall 56 of the device 10, and has a bore 204 adapted to provide clearance for the output end portion 25 of the first output shaft 23 which does not make driving engagement with the reamer driver 14.

The driven shaft 19 of the reamer driver 14 projects through and is rotatably mounted in a cavity defined in the frame 53 by a ball bearing 205. Like the second output shaft 24, the driven shaft 19 has a through central opening, and has two tapered projections 71 on its end in the projecting portion 49 adapted to be engaged by similar projections 63 on the second output shaft 24 as has previously been described.

A drive gear 207 is fixed on (as by being integrally formed with) the end portion of the driven shaft 19 opposite the projections 71. A ring gear 208 is fixed on the frame 53 coaxially around the drive gear 207. A plurality of planetary gears 209 having teeth engaged with the teeth of the drive gear 207 and ring gear 208 are positioned around the driver gear 207, and are rotatably supported on a carrier 210 having a through central opening, which carrier 210 is rotatably mounted on the frame 53 by two ball bearings 211. The end of the carrier 210 opposite the planetary gears 209 provides an inner portion 212 of a special chuck assembly 214 similar to the chuck assembly 186 for engaging tools such as the reamer 15 shown in phantom outline in FIG. 15 which have driven ends of the types commercially designated "Hudson" or "Zimmer" TM style. The inner portion 212 has through radially extending passageways from its outer surface to its central opening in which are positioned locking balls 218. Also included in the chuck assembly 214 is a sleeve-like outer portion 220 to which are fixed opposed inwardly projecting pins 222 received in opposed longitudinal slots in the inner portion 212 and engaging the end of a compressed coil spring 224 centrally located in the carrier 210 and having its opposite end supported adjacent an end of the driven shaft 19 journaled in the carrier 210 to bias the sleeve-like outer portion 220 to a position at which its inner surface engages the surfaces of the locking balls 218 and can lock the balls 218 in engagement with recesses in the driven end of the reamer 15. The sleeve-like outer portion 220 can be manually moved axially relative to the driven shaft 19 to further compress the spring 224 and position grooves 226 on its inner surface adjacent the locking balls 218 so that they may move radially outwardly out of recesses in the reamer 15 and the reamer 15 may be removed or inserted.

The reamer driver 14, is used in the same way as the univesal chuck 13 described above, the only significant difference being that the output speed at the chuck assembly 214 will be significantly less for a given speed at the second output shaft 24 of the device 10 as is more appropriate for driving a reamer due to the gear reduction caused by the gears 207, 208 and 209 (e.g., about a 4/1 gear reduction).

Preferably the main portion 76 of the frame 20 is of aluminum treated to form a dark colored (e.g., dark gray) hard anodized layer 300 (FIG. 16) defining the surface of the aluminum, and having a dark colored (e.g., black) coating of tetrafluoroethylene over the anodized layer. A method has been found for forming crisp white indicia (e.g., printed tradenames or instructions) on the aluminum frame 20 after forming the anodized layer 300 by removing with a laser precise predetermined portions 304 of the anodized layer 300 in the shape of the indicia. This results in forming a white aluminum oxide coating 306 on the frame 20 on an aluminum surface 302 exposed by the laser-induced removal of the predetermined portions 304 of the dark anodized layer 300. The white aluminum oxide coating 306 forms crisp white indicia which are very clearly visible through the remainder 308 of the dark coating.

The present invention has now been described with reference to one embodiment of the device and several tool embodiments. It will be apparent to those skilled in the art that many changes can be made in the embodiment described without departing from the scope of the present invention. Thus the scope of the present invention should not be limited to the structures described in this application, but only by structures described by the language of the claims and the equivalents of those structures.

We claim:

1. A method for forming crisp white indicia on an aluminum housing comprising the steps of:
    forming a dark colored hard anodized layer defining a surface of the housing;
    removing with a laser precise predetermined portions of the anodized layer in the shape of the indicia and forming by the removal a white aluminum oxide coating on a surface exposed by the laser-induced removal, the oxide coating forming crisp white indicia visible through the remainder of the anodized layer.

2. A method according to claim 1 including the further step of coating the housing over the dark colored hard anodized layer with a dark colored coating of tetrafluoroethylene and said removing step removes precise predtermined portions of the tetrafluoroethylene coating and the anodized layer.

3. A method according to claim 1 wherein the step of removing portions of the anodized layer includes removing with the laser the entire anodized layer in precise predetermined indicia-shaped areas.

* * * * *

UNITED STATES PATENT AND TRADEMARK OFFICE
CERTIFICATE OF CORRECTION

PATENT NO. : 4,806,730
DATED : February 21, 1989
INVENTOR(S) : Charles E. Alexson It is certified that error appears in the above-identified patent and that said Letters Patent is hereby corrected as shown below:

Col. 6, line 21, delete "46" and insert --45--.

Col. 7, line 37, delete "wallmeans" and insert --wall means--.

Col. 14, line 21, delete "predtermined" and insert --predetermined--.

Signed and Sealed this

Twenty-eighth Day of November 1989

Attest:

JEFFREY M. SAMUELS

*Attesting Officer*    *Acting Commissioner of Patents and Trademarks*